(12) United States Patent
Nagahara et al.

(10) Patent No.: US 11,383,092 B2
(45) Date of Patent: Jul. 12, 2022

(54) REACTIVE GAS APPLICATION APPARATUS

(71) Applicant: SEKISUI CHEMICAL CO., LTD., Osaka (JP)

(72) Inventors: Yu Nagahara, Kyoto (JP); Yoshishige Takikawa, Osaka (JP); Takaya Oshita, Nagareyama (JP); Tsuyoshi Uehara, Nara (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 231 days.

(21) Appl. No.: 16/491,324

(22) PCT Filed: Aug. 31, 2018

(86) PCT No.: PCT/JP2018/032402
§ 371 (c)(1),
(2) Date: Sep. 5, 2019

(87) PCT Pub. No.: WO2019/045054
PCT Pub. Date: Mar. 7, 2019

(65) Prior Publication Data
US 2020/0030621 A1    Jan. 30, 2020

(30) Foreign Application Priority Data

Aug. 31, 2017 (JP) .............................. JP2017-166987

(51) Int. Cl.
*A61N 1/44* (2006.01)
*A61C 19/06* (2006.01)
(Continued)

(52) U.S. Cl.
CPC ................ *A61N 1/44* (2013.01); *A61C 19/06* (2013.01); *F21V 5/04* (2013.01); *F21V 33/0068* (2013.01);
(Continued)

(58) Field of Classification Search
CPC .. A61N 1/44; A61C 19/06; F21V 5/04; F21V 33/0068
See application file for complete search history.

(56) References Cited

U.S. PATENT DOCUMENTS

2001/0032000 A1* 10/2001 Dotan ....................... A61F 7/02
607/96
2011/0101862 A1* 5/2011 Koo ................... H01J 37/32449
315/111.21
(Continued)

FOREIGN PATENT DOCUMENTS

JP    2012-528452    11/2012
JP    5441066        3/2014
(Continued)

OTHER PUBLICATIONS

International Search Report dated Oct. 9, 2018 in International (PCT) Application No. PCT/JP2018/032402.
(Continued)

*Primary Examiner* — Bryon T Gyllstrom
(74) *Attorney, Agent, or Firm* — Wenderoth, Lind & Ponack, L.L.P.

(57) ABSTRACT

The present invention provides a reactive gas application apparatus capable of easily and surely applying a reactive gas to a target object. The reactive gas application apparatus (100) includes: a plasma generating unit (12), a nozzle (1) for discharging a reactive gas activated by plasma generated in the plasma generation unit (12), and a light source unit (50) for emitting light toward a position ahead of a tip of the nozzle (1). The reactive gas application apparatus preferably further includes a control unit for synchronizing plasma generation in the plasma generation unit and light emission in the light source unit.

8 Claims, 7 Drawing Sheets

(51) Int. Cl.
    *F21V 5/04*     (2006.01)
    *F21V 33/00*     (2006.01)
    *F21Y 113/13*     (2016.01)
    *F21Y 115/10*     (2016.01)
    *A61C 1/08*     (2006.01)

(52) U.S. Cl.
    CPC ............ *A61C 1/088* (2013.01); *A61C 19/063* (2013.01); *F21Y 2113/13* (2016.08); *F21Y 2115/10* (2016.08)

(56) References Cited

U.S. PATENT DOCUMENTS

| | | | | |
|---|---|---|---|---|
| 2011/0183284 A1* | 7/2011 | Yamanaka | ............ | A61C 17/02 433/32 |
| 2013/0068732 A1* | 3/2013 | Watson | ................ | H01J 37/321 219/121.5 |
| 2014/0188097 A1 | 7/2014 | Watson et al. | | |
| 2014/0188195 A1* | 7/2014 | Jacofsky | ................ | A61B 90/06 607/88 |
| 2016/0106993 A1* | 4/2016 | Watson | ................ | A61M 25/00 604/24 |
| 2016/0271419 A1* | 9/2016 | Varghese | ............. | A61B 18/203 |
| 2016/0287310 A1* | 10/2016 | Nettesheim | .......... | A61B 18/042 |
| 2018/0008754 A1* | 1/2018 | Swift | ...................... | A61M 1/76 |
| 2020/0038530 A1* | 2/2020 | Yildirim | ............. | A61N 5/0625 |
| 2020/0306001 A1* | 10/2020 | Silver | ....................... | F21L 4/00 |

FOREIGN PATENT DOCUMENTS

| | | |
|---|---|---|
| JP | 2014-204925 | 10/2014 |
| JP | 2017-500078 | 1/2017 |
| JP | 2017-50267 | 3/2017 |
| WO | 2006/087547 | 8/2006 |
| WO | 2007/058043 | 5/2007 |
| WO | 2010/138102 | 12/2010 |
| WO | 2015/071099 | 5/2015 |
| WO | 2017/037885 | 3/2017 |
| WO | 2017/037886 | 3/2017 |

OTHER PUBLICATIONS

Andrei Vasile Nastuta et al., "Stimulation of wound healing by helium atmospheric pressure plasma treatment", Journal of Physics D: Applied Physics, IOP Publishing, 2011, vol. 44.
Communication pursuant to Article 94(3) EPC dated Dec. 21, 2021 in European Patent Application No. 18 851 245.3.

* cited by examiner

REACTIVE GAS APPLICATION APPARATUS

TECHNICAL FIELD

The present invention relates to a reactive gas application apparatus.

Priority is claimed on Japanese Patent Application No. 2017-166987, filed Aug. 31, 2017, the contents of which are incorporated herein by reference.

BACKGROUND ART

Conventionally, apparatuses for medical use such as dental treatment are known, which apply plasma to an affected part of a patient in an attempt to heal wounds and the like.

For example. Patent Document 1 and Non-Patent Document 1 disclose a plasma jet application apparatus provided with an instrument (application instrument) for applying a plasma jet. The plasma jet application apparatus generates plasma, and applies the generated plasma together with reactive species to a target object, in which the reactive species are generated by reaction of the plasma with the gas present within or around the plasma.

Further, as an apparatus similar to the plasma jet application apparatus, a reactive gas application apparatus is known. The reactive gas application apparatus generates reactive gas (active species) such as active oxygen or active nitrogen by plasma generated in the application instrument, and discharges the reactive gas from the nozzle of the application instrument to apply the reactive gas to an affected area of a patient.

DESCRIPTION OF PRIOR ART

Patent Document

Patent Document 1: Japanese Patent Granted Publication No. 5441066

Non-Patent Document

Non-Patent Document 1: Andrei Vasile Nastuta et al., "Journal of Physics D: Applied Physics", UK and USA, vol. 44, IOP Publishing, Feb. 21, 2011, 105204

DISCLOSURE OF INVENTION

Problems to be Solved by the Invention

However, in the reactive gas application apparatus, since the generated reactive gas is colorless, it is difficult to visually recognize the reactive gas discharged from the nozzle. For this reason, in the conventional reactive gas application apparatus, a user is required to manipulate the application instrument with his or her intuition so that the reactive gas hits the affected area. Therefore, with the conventional reactive gas application apparatus, it is not easy to ensure that the reactive gas is applied to the affected area.

The purpose of the present invention is to provide a reactive gas application apparatus capable of easily and surely applying a reactive gas to a target object.

Means to Solve the Problems

The embodiments of the present invention are as follows.
[1] A reactive gas application apparatus including: a plasma generating unit, a nozzle for discharging a reactive gas activated by plasma generated in the plasma generation unit, and a light source unit for emitting light toward a position ahead of a tip of the nozzle.
[2] The reactive gas application apparatus according to [1], which further include a control unit for synchronizing plasma generation in the plasma generation unit and light emission in the light source unit.
[3] The reactive gas application apparatus according to [1] or [2], wherein the light source unit emits light having a focal point.
[4] The reactive gas application apparatus according to any one of [1] to [3], wherein the light source unit comprises a light emitter and a condenser lens positioned in a light emission direction of the light emitter.
[5] The reactive gas application apparatus according to any one of [1] to [4] which has two or more light source units.
[6] The reactive gas application apparatus according to [5]), wherein the two or more light source units emit respectively different colored lights, and the different colored lights overlap at a predetermined position.
[7] The reactive gas application device according to any one of [1] to [6], which is a medical therapeutic apparatus.

Effect of the Invention

According to the reactive gas application apparatus of the present invention, a reactive gas can be easily and surely applied to a target object.

DESCRIPTION OF THE EMBODIMENTS

First Embodiment

Explanations are made below with respect to a first embodiment of the reactive gas application apparatus of the present invention.

The reactive gas application apparatus of the present embodiment is one that generates a plasma, brings a gas into contact with the plasma to generate a reactive gas, and applies the reactive gas to a target object.

Figure 1:
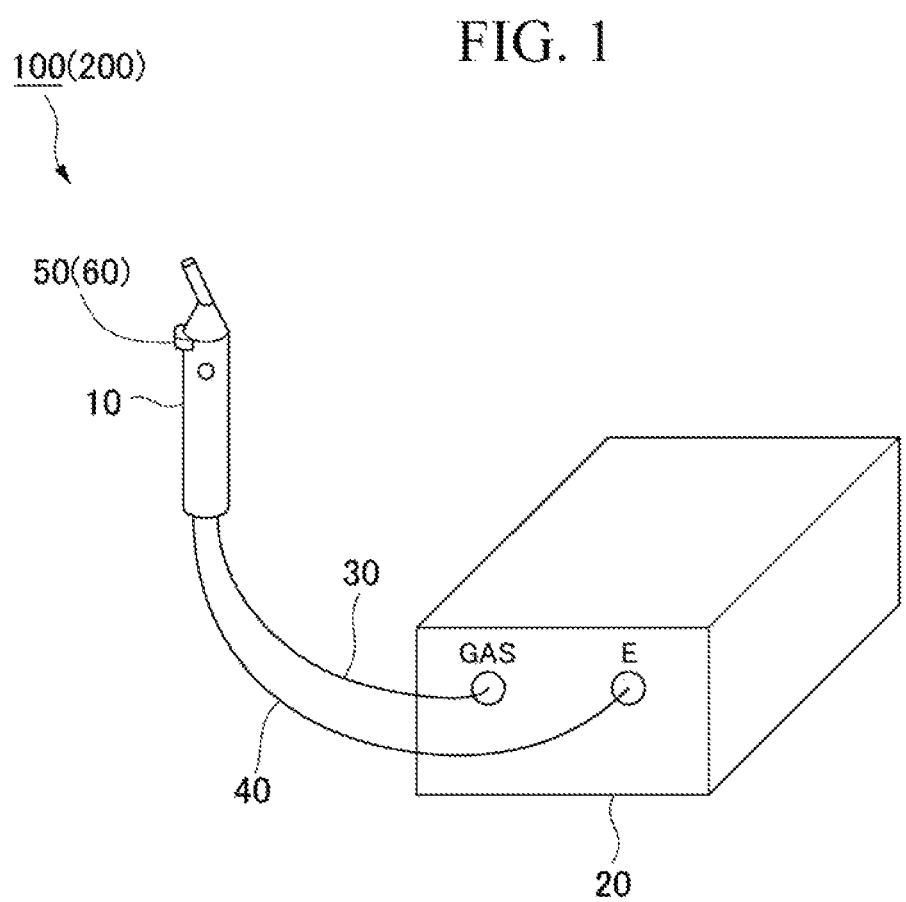
FIG. 1 is a schematic view of a reactive gas application apparatus according to the first and second embodiments of the present invention.

The reactive gas application apparatus 100 shown in FIG. 1 includes an application instrument 10, a power supply unit 20, a gas conduit 30, and an electrical wiring 40.

The gas conduit 30 connects the application instrument 10 with the power supply unit 20. The electrical wiring 40 connects the application instrument 10 with the power supply unit 20.

In the present embodiment, the gas conduit 30 and the electric wiring 40 are provided independently from each other, but the gas conduit 30 and the electric wiring 40 may be integrated.

The power supply unit 20 is connected to a plasma generating gas supply source (not shown). The gas pipe 30 may be directly connected to the supply source of the plasma generating gas without passing through the power supply unit 20. However, the gas pipe 30 is preferably configured as shown in FIG. 1 from the viewpoint of handling of the reactive gas application apparatus 100, and the like.

The power supply unit 20 is connected to, for example, a power supply (not shown) such as a 100 V power supply.

Figure 2:
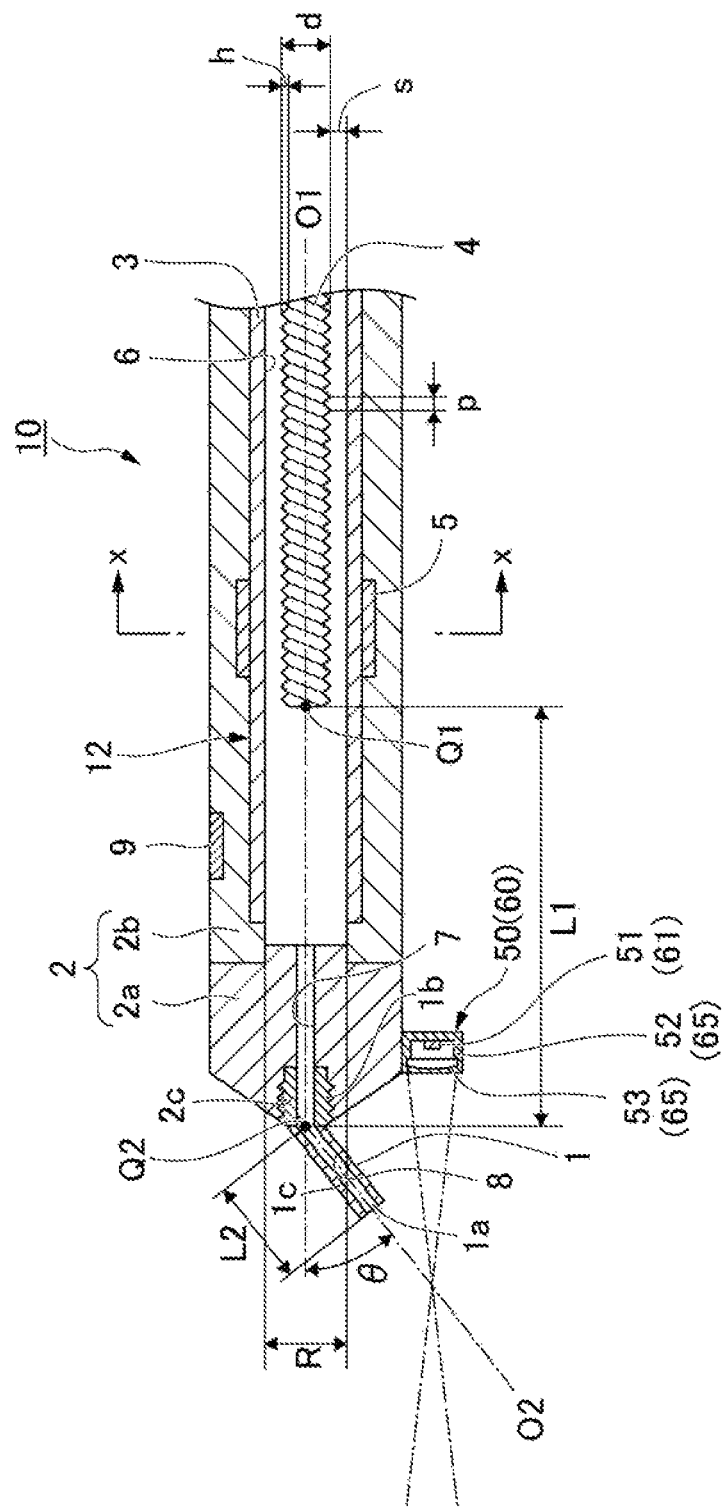
FIG. 2 is a partial cross-sectional view of an application instrument included in a reactive gas application apparatus according to the first and second embodiments of the present invention.

FIG. 2 is a cross-sectional view (longitudinal section) showing a plane along the axis of the application instrument 10.

As shown in FIG. 2, the application instrument 10 includes an elongated cowling 2, a nozzle 1 protruding from the tip of the cowling 2, a plasma generating unit 12 provided in the cowling 2, and a light source unit 50.

The cowling 2 includes a cylindrical body 2b and a head 2a covering the tip of the body 2b. The body 2b is not limited to that of a cylindrical shape, and may be of a polygonal tube shape such as a square tube shape, a hexagonal tube shape, an octagonal tube shape or the like.

The head 2a gradually narrows toward the tip thereof. That is, the head 2a in the present embodiment has a conical shape. The head 2a is not limited to that of a conical shape, and may be of a polygonal cone shape such as a quadrangular pyramid shape, a hexagonal pyramid shape, an octagonal pyramid shape or the like.

The head 2a has a fitting hole 2c at its tip. The fitting hole 2c is a hole for receiving the nozzle 1. The nozzle 1 is detachably attached to the head 2a. Symbol O1 denotes the tube axis of the body 2b. A first reactive gas flow path 7 extending in the tube axis O1 direction is provided inside the head 2a.

A switch 9 is provided on the outer peripheral surface of the body 2b.

Figure 3:
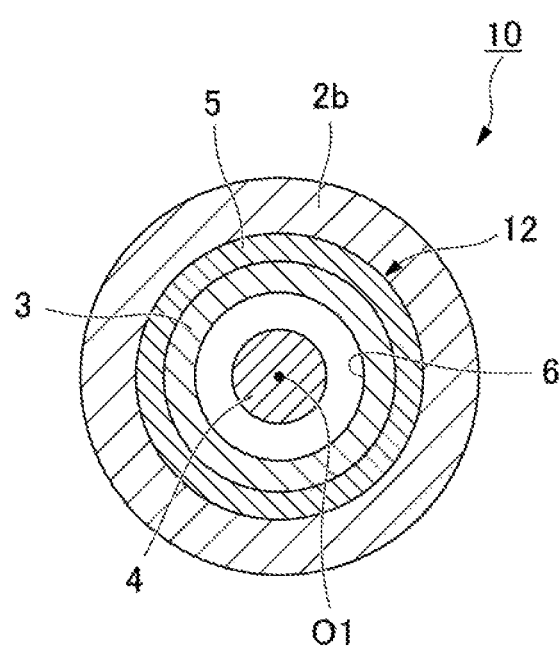
FIG. 3 is a cross sectional view of the application instrument of FIG. 2 as viewed from the arrow direction of the x-x line of FIG. 2.

As shown in FIGS. 2 and 3, the plasma generating unit 12 includes a tubular dielectric 3, an inner electrode 4, and an outer electrode 5.

The tubular dielectric 3 is a cylindrical member extending in the tube axis O1 direction. The tubular dielectric 3 has in its inside a gas flow path 6 extending in the tube axis O1 direction. The gas flow path 6 communicates with a first reactive gas flow path 7. The tube axis O1 coincides with the tube axis of the tubular dielectric 3.

In the tubular dielectric 3, an inner electrode 4 is provided. The inner electrode 4 is a substantially columnar member extending in the lube axis O1 direction. The inner electrode 4 is spaced apart from the inner surface of the tubular dielectric 3.

On the outer peripheral surface of the tubular dielectric 3, an outer electrode 5 extending along the inner electrode 4 is provided. The outer electrode 5 is an annular electrode that circulates along the outer peripheral surface of the tubular dielectric 3.

As shown in FIG. 3, the tubular dielectric 3, the inner electrode 4, and the outer electrode 5 are positioned concentrically around the tube axis O1.

In the present embodiment, the outer peripheral surface of the inner electrode 4 and the inner peripheral surface of the outer electrode 5 face each other through the tubular dielectric 3.

The nozzle 1 includes a base 1b fitted in the fitting hole 2c, and a discharge tube 1c protruding from the base 1b. The base 1b and the discharge tube 1c are integrated with each other. The nozzle 1 has in its inside a second reactive gas flow path 8. The nozzle 1 has an outlet 1a at its tip end. The second reactive gas flow path 8 and the first reactive gas flow path 7 communicate with each other.

The material of the body 2b is not particularly limited, but is preferably an insulating material. Examples of the insulating material include thermoplastic resins such as polyethylene, polypropylene, polyvinyl chloride, polystyrene, acrylonitrile-butadiene-styrene resin (ABS resin); and thermosetting resins such as a phenol resin, a melamine resin, a urea resin, an epoxy resin, an unsaturated polyester resin and a silicone resin.

The size of the body 2b is not particularly limited, and may be such a size that allows the body 2b to be easily grasped with fingers.

The material of the head 2a is not particularly limited, and may or may not be an insulating material. The material of the head 2a is preferably a material excellent in abrasion resistance and corrosion resistance. As an example of such a material excellent in abrasion resistance and corrosion resistance, a metal such as stainless steel can be mentioned. The materials of the head 2a and the body 2b may be the same or different.

The size of the head 2a can be decided in consideration of the use of the reactive gas application device 100 and the like. For example, when the reactive gas application apparatus 100 is an apparatus for an intraoral treatment, the size of the head 2a is preferably set to be such a size that allows the apparatus 100 to be inserted into an oral cavity.

As a material of the tubular dielectric 3, a dielectric material used for a known plasma generator can be employed. Examples of the material of the tubular dielectric 3 include glass, ceramics, synthetic resins, and the like. The dielectric constant of the tubular dielectric 3 is preferably as low as possible.

The inner diameter R of the tubular dielectric 3 can be appropriately decided in consideration of the outer diameter d of the inner electrode 4. The inner diameter R is set such that a distance s (described later) falls within a predetermined range.

The inner electrode 4 includes a shaft portion extending in the tube axis O1 direction and a screw thread on the outer peripheral surface of the shaft portion. The shaft portion may be solid or hollow. Of these, a solid shaft portion is more preferable. The solid shaft portion allows easy processing and improves mechanical durability. The screw thread of the inner electrode 4 is a helical screw thread that circulates in the circumferential direction of the shaft portion. The shape of the inner electrode 4 is the same as that of a screw or a bolt.

The screw thread on the outer peripheral surface of the inner electrode 4 allows the electric field at the tip of the screw thread to be locally enhanced, thereby lowering the discharge inception voltage. Therefore, plasma can be generated and maintained with less electric power.

The outer diameter d of the inner electrode 4 is appropriately decided in consideration of the application of the reactive gas application apparatus 100 (that is, the size of the application instrument 10) and the like. When the reactive gas application apparatus 100 is an apparatus for an intraoral treatment, the outer diameter d is preferably 0.5 to 20 mm, more preferably 1 to 10 mm. When the outer diameter d is not less than the above lower limit value, the inner electrode can be easily manufactured. Further, the outer diameter d of not less than the above lower limit value increases the surface area of the inner electrode 4, whereby plasma can be generated more efficiently, and healing and the like can be further promoted. When the outer diameter d is not more than the above upper limit value, plasma can be generated more efficiently and the healing and the like can be further promoted without excessively increasing the size of the application instrument 10.

The height h of the screw thread of the inner electrode 4 can be appropriately decided in consideration of the outer diameter d of the inner electrode 4.

The thread pitch p of the inner electrode 4 can be appropriately decided in consideration of the length and outer diameter d of the inner electrode 4, find the like.

The material constituting the inner electrode 4 is not particularly limited as long as the material is electrically conductive, and metals used for electrodes of known plasma generating apparatuses can be used. Examples of the material of the inner electrode 4 include metals such as stainless steel, copper and tungsten, carbon, and the like.

The inner electrode 4 preferably has the same specification as any of the metric screw threads complying with JIS B 0205: 2001 (M2, M2.2, M2.5, M3, M3.5, etc.), the metric trapezoidal screw threads complying with JIS B 2016: 1987 (Tr8×1.5, Tr9×2, Tr9×1.5, etc.), the unified coarse screw threads complying with JIS B 0206: 1973 (No. 1-64 UNC, No. 2-56 UNC, No. 3-48 UNC, etc.), and the like. The inner electrode 4 having the same specification as those standardized products is advantageous in terms of cost.

The distance s between the other surface of the inner electrode 4 and the inner surface of the tubular dielectric 3 is preferably 0.05 to 5 mm, more preferably 0.1 to 1 mm. When the distance s is not less than the above lower limit value, a desired amount of plasma generating gas is allowed to flow easily. When the distance s is not more than the above upper limit value, plasma can be generated more efficiently and the temperature of the reactive gas can be lowered.

The material constituting the outer electrode 5 is not particularly limited as long as the material is electrically conductive, and metals used for electrodes of known plasma generating apparatuses can be used. Examples of the material of the outer electrode 5 include metals such as stainless steel, copper and tungsten, carbon, and the like.

The material of the nozzle 1 is not particularly limited, and may or may not be an insulating material. The material of the nozzle 1 is preferably a material excellent in abrasion resistance and corrosion resistance. As an example of such a material excellent in abrasion resistance and corrosion resistance, a metal such as stainless steel can be mentioned.

The length (that is, the distance L2) of the flow path in the discharge tube 1c can be appropriately decided in consideration of the use of the reactive gas application apparatus 100 or the like.

The opening diameter of the outlet 1a is preferably, for example, 0.5 to 5 mm. When the opening diameter is not less than the above lower limit value, the pressure loss of the reactive gas can be suppressed. When the opening diameter is not more than the above upper limit value, the flow rate of the discharged reactive gas can be increased to promote healing and the like.

The discharge tube 1c is bent with respect to the tube axis O1.

The angle θ formed between the tube axis O2 of the discharge tube 1c and the tube axis O1 can be decided in consideration of the use of the reactive gas application apparatus 100 and the like.

The sum of the distance L1 from the tip end Q1 of the inner electrode 4 to the tip end Q2 of the head 2a and the distance L2 from the tip end Q2 to the outlet 1a (that is, a distance from the inner electrode 4 to the outlet 1a) is appropriately decided in consideration of the size of the reactive gas application apparatus 100, the temperature of a surface to which the reactive gas is applied (target surface), and the like. When the sum of the distance of L1 and the distance L2 is large, the temperature of the target surface can be lowered. When the sum of the distance of L1 and the distance L2 is small, the radical concentration of the reactive gas can be further increased, and the effects of cleaning, activation, healing, etc. on the target surface can be further enhanced. The tip end Q2 is an intersection point between tire tube axis O1 and the tube axis O2.

The power supply unit 20 is a device that supplies electricity to the application instrument 10. The power supply unit 20 in the present embodiment is provided with a pump that sends a plasma generating gas to the application instrument 10 via the gas conduit 30. The power supply unit 20 can control the voltage to be applied between the outer electrode 5 and the inner electrode 4, and the frequency thereof.

The power supply unit 20 may not have a pump. In such case, a pump may be provided independently of the power supply unit 20. Alternatively, the plasma generating gas may also be supplied to the application instrument 10 by pressure at the plasma generating gas supply source.

The gas conduit 30 is a path for supplying the plasma generating gas from the power supply unit 20 to the application instrument 10. The gas conduit 30 is connected to the rear end of the tubular dielectric 3 of the application instrument 10. The material of the gas conduit 30 is not particularly limited, and a material used for known gas pipes can be used. Concerning a material of the gas conduit 30, a resin pipe, a rubber tube and the like can be exemplified, and a material having flexibility is preferable.

The electrical wiring 40 is a wiring for supplying electricity from the power supply unit 20 to the application instrument 10. The electric wiring 40 is connected to the inner electrode 4, the outer electrode 5 and the switch 9 of the application instrument 10. The material of the electric wiring 40 is not particularly limited, and a material used for a known electric wiring can be employed. As examples of the material of the electric wiring 40, a metal lead wire covered with an insulating material and the like can be mentioned.

Figure 4:
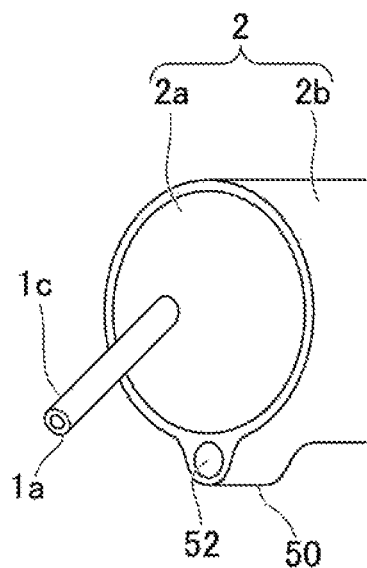
FIG. 4 is a perspective view showing a tip of the application instrument in the first embodiment.

As shown in FIGS. 2 and 4, the reactive gas application apparatus 100 of the present embodiment includes a light source unit 50 on the outside of the cowling 2. As for the installation position of the light source unit 50 on the outside of the cowling 2, the light source unit 50 is positioned in a direction in which the discharge tube 1c is bent when the application instrument 10 is viewed from the side of the nozzle 1 along the direction of the tube axis O1.

The light source unit 50 in the present embodiment includes a light emitting diode 51, a condenser lens 52 and a holder 53. The condenser lens 52 is located in the light emitting direction of the light-emitting diode 51. The holder 53 holds the light emitting diode 51 and the condenser lens 52.

In the present embodiment, the light emitting diode 51 is the light emitter.

The light source unit 50 generates light (guide light) that illuminates a predetermined direction. The guide light has a focal point F at a predetermined distance from the tip of the nozzle 1. In the present embodiment, the focal point F is located on the tube axis O2. The focal point F is a position suitable for the application of the reactive gas. That is, at the focal point F, the reactive gas exhibits characteristics suited for the purpose. For example, at the focal point F, the reactive gas has a composition of active species suitable for medical treatment. Also, for example, at the focal point F, the reactive gas has a temperature suitable for application. Therefore, a user of the reactive gas application apparatus 100 can easily apply a reactive gas of suitable quality to an affected area by placing the focal point of the guide light on the affected area. The distance from the tip of the nozzle to the focal point may be referred to as a "preferred distance".

As the light emitting diode 51, a known light emitting diode that emits visible light (light having a wavelength of about 360 nm to about 830 nm can be used without any limitation. However, when using the reactive gas application apparatus 100 for treatment of an affected part, a white diode emitting white light and a red diode emitting red light are not preferable. Usually, when treating an affected area, white light is used to illuminate an affected area to enhance the visibility of the affected area; therefore, it is difficult to visually recognize the application position with white light as the guide light. Further, since the affected area may be bleeding, it is difficult to visually recognize the application position with red light having a color close to that of blood.

For these reasons, the light emitting diode 51 is preferably a light emitting diode that emits light other than white light and red light. For example, the light emitting diode 51 is preferably one that emits light such as green light, yellow green light, blue light, yellow light and the like.

In the present embodiment, the application instrument 10 may include two or more light emitting diodes of different color tones, and may have a mechanism for adjusting the color tone or the illumination intensity of the guide light according to the target surface.

The light emitted from the application instrument 10 needs to contain visible light, but the application instrument 10 may be configured to emit invisible light such as infrared light and ultraviolet light as well in order to achieve a desired therapeutic effect. For example, ultraviolet radiation is known to have a therapeutic effect on specific skin diseases. Further, photothermal chemotherapy and photodynamic therapy are known which respectively utilize the exothermic action of a dye having an absorption wavelength in the infrared region and the active oxygen generation action (PDT effect) of the dye. Therefore, the above configuration may produce synergetic effect of application of reactivation gas and irradiation of the invisible light.

The condenser lens 52 has at least a convex lens and converges the light from the light emitting diode 51. The convex lens may be a spherical lens or an aspheric lens. The diameter of the convex lens, the curvature of the curved surface of the convex lens, and the thickness of the convex lens can be appropriately selected according to the preferred distance from the nozzle tip.

The holder 53 is a part that holds the light emitting diode 51 and the condenser lens 52. The holder 53 fixes the light emitting diode 51 and the condenser lens 52 such that the condenser lens 52 is positioned in the light emitting direction of the light emitting diode 51. In the present embodiment, the light emitting diode 51 and the condenser lens 52 are fitted in a space within the holder 53. In the present embodiment, the holder 53 is integral with the application instrument 10.

As a material of the holder 53, the same material as that of the body 2b of the application instrument 10 can be used. The material of the holder 53 may be the same as or different from that of the body 2b of the application instrument 10.

The holder 53 may be provided with a lens angle adjustment mechanism that adjusts the angle of the condenser lens 52. When the holder 53 is provided with a lens angle adjustment mechanism, the direction of the light path of the guide light can be adjusted. Thus, even if the preferred distance changes, the guide light can be easily adjusted to indicate the preferred distance.

Figure 5:
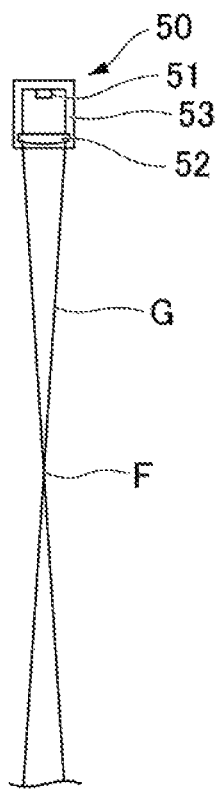
FIG. 5 is a schematic view showing a light source unit in the first embodiment and light emitted by the light source unit.

In the light source unit 50 in the present embodiment, the light emitted from the light emitting diode 51 is converged by the condenser lens 52. For this reason, as shown in FIG. 5, the diameter of the guide light G emitted from the light source unit 50 gradually decreases until reaching the focal point F, and gradually increases after passing the focal point F.

In the present embodiment, the focal point F of the guide light G is located approximately at a preferred distance from the tip of the nozzle. The distance from the nozzle tip to the focal point F is adjusted by the combination of the arrangement of the light source unit 50, the diameter, curvature and thickness of the curved surface of the condenser lens 52, and the like.

As for the light source unit 50 in the present embodiment, it is preferable to synchronize the light emission of the guide light with the discharge of the reactive gas. When the emission of the guide light is synchronized with the discharge of the reactive gas, the emission of the guide light can be regarded as indicating that the transparent and invisible reactive gas is being discharged from the outlet 1a.

When it is intended to synchronize the emission of the guide light with the discharge of the reactive gas, the reactive gas application apparatus 100 further includes a control unit (not shown).

Examples of parts usable as the control unit include one that detects the electric conduction for applying a voltage between the inner electrode 4 and the outer electrode 5, and allows the light emitting diode 51 to emit light while the electric conduction is being detected. Another example of the control unit is a part that detects plasma generated in the internal space of the application instrument 10, and allows the light omitting diode 51 to emit light while the plasma generation is being detected.

Next, a method of using the reactive gas application apparatus 100 will be described.

First, the plasma generating gas is supplied to the application instrument 10 from the plasma generating gas supply source via the power supply unit 20.

The plasma generating gas supplied to the application instrument 10 is allowed to flow into the hollow portion of the tubular dielectric 3 from the rear end of the tubular dielectric 3.

Then, electricity is supplied from the power supply unit 20 to the application instrument 10 to apply voltage between the inner electrode 4 and the outer electrode 5. The plasma generating gas introduced into the hollow portion of the tubular dielectric 3 is ionized at a position where the inner electrode 4 and the outer electrode 5 face each other, and turned into plasma.

In the present embodiment, the inner electrode 4 and the outer electrode 5 face each other in a direction orthogonal to the flowing direction of the plasma generating gas. Plasma generated at a position where the outer peripheral surface of the inner electrode 4 and the inner peripheral surface of the outer electrode 5 face each other is allowed to pass through the gas flow path 6, the first reactive gas flow path 7, and the second reactive gas flow path 8 in this order. In this process, the plasma flows while changing the gas composition, and becomes a reactive gas containing active species such as radicals.

The generated reactive gas is discharged from the outlet 1a. The discharged reactive gas further activates a part of the gas in the vicinity of the outlet 1a into active species. The reactive gas containing these active species is applied to a target object.

Examples of the target object include cells, living tissues, and whole bodies of organisms.

Examples of the living tissue include various organs such as internal organs, epithelial tissues covering the body surface and the inner surfaces of the body cavity, periodontal tissues such as gums, alveolar bone, periodontal ligament and cementum, teeth, bones and the like.

The whole bodies of organisms may be any of mammals such as humans, dogs, cats, pigs and the like; birds; fishes and the like.

Examples of the plasma generating gas include noble gases such as helium, neon, argon and krypton; nitrogen; and the like. With respect to these gases, a single type thereof may be used individually or two or more types thereof may be used in combination.

The plasma generating gas preferably contains nitrogen gas as a main component. Here, the nitrogen gas being contained as a main component means that the amount of the nitrogen gas contained in the plasma generating gas is more than 50% by volume. That is, the amount of the nitrogen gas contained in the plasma generating gas is preferably more than 50% by volume, more preferably 70% by volume or more, still more preferably 90 to 100% by volume. The gas component other than nitrogen in the plasma generating gas is not particularly limited, and examples thereof include oxygen and a noble gas.

When the reactive gas application apparatus 100 is an apparatus for an intraoral treatment, the plasma generating gas to be introduced into the tubular dielectric 3 preferably has an oxygen concentration of 1% by volume or less. When the oxygen concentration is not more than the upper limit value, generation of ozone can be suppressed.

The flow rate of the plasma generating gas introduced into the tubular dielectric 3 is preferably 1 to 10 L/min.

When the flow rate of the plasma generating gas introduced into the tubular dielectric 3 is not less than the above lower limit value, it becomes easy to suppress the temperature rise of a target surface of the target object. When the flow rate is not more than the above upper limit value, the cleaning, activation or healing of the target object can be further promoted.

The alternating voltage applied between the inner electrode 4 and the outer electrode 5 is preferably 5 kVpp or more and 20 kVpp or less. Here, the unit "Vpp (Volt peak to peak)" representing the alternating voltage means a potential difference between the highest value and the lowest value of the alternating voltage waveform.

When the applied alternating voltage is not more than the above upper limit value, the temperature of the generated plasma can be kept low. When the applied alternating voltage is not less than the above lower limit value, plasma can be generated more efficiently.

The frequency of the alternating voltage applied between the inner electrode 4 and the outer electrode 5 is preferably 0.5 kHz or more and less than 20 kHz, more preferably 1 kHz or more and less than 15 kHz, even more preferably 2 kHz or more and less than 10 kHz, particularly preferably 3 kHz or more and less than 9 kHz, and most, preferably from 4 kHz or more and less than 8 kHz.

When the frequency of the alternating voltage is less than the above upper limit value, the temperature of the generated plasma can be suppressed low. When the frequency of the alternating voltage is not less than the above lower limit value, plasma can be generated more efficiently.

The temperature of the reactive gas discharged from the outlet 1a of the nozzle 1 is preferably 50° C. or less, more preferably 45° C. or less, and even more preferably 40° C. or less.

When the temperature of the reactive gas discharged from the outlet 1a of the nozzle 1 is not more than the upper limit value, the temperature of the target surface (i.e., temperature around the local point F) can be easily adjusted to 40° C. or less. By keeping the temperature of the target surface at 40° C. or less, stimulus to the target surface can be reduced even when the target surface is an affected part.

The lower limit value of the temperature of the reactive gas discharged from the outlet 1a of the nozzle 1 is not particularly limited, and is, for example, 10° C. or more.

The temperature of the reactive gas is a temperature value of the reactive gas at the outlet 1a measured by a thermocouple.

The distance (application distance) from the outlet 1a to the target surface is preferably, for example, 0.01 to 10 mm. When the application, distance is not less than the above lower limit value, the temperature of the target surface can be lowered, and the stimulus to the target surface can be further reduced. When the application distance is not more than the above upper limit value, the effect of healing and the like can be further enhanced. That is, the preferable distance is 0.01 to 10 mm. The distance from the light source unit 50 to the target surface is not particularly limited as long as a sufficient amount of light can be secured on the target surface, but the distance is preferably 5 to 100 mm, and more preferably 10 to 50 mm.

The temperature of the target surface positioned at a distance of 1 mm or more and 10 mm or less from the outlet 1a is preferably 40° C. or less. By setting the temperature of the target surface to 40° C. or less, stimulus to the target surface can be reduced. The lower limit value of the temperature of the target surface is not particularly limited, and is, for example, 10° C. or more.

The temperature of the target surface is adjusted by controlling the alternating voltage applied between the inner electrode 4 and the outer electrode 5, the discharge amount of the reactive gas, the distance front the tip end Q1 of the inner electrode 4 to the outlet 1a, and the like, some or all of which are controlled in combination.

The temperature of the target surface can be measured by a thermocouple.

Examples of the active species (radicals etc.) contained in the reactive gas include hydroxyl radicals, singlet oxygen, ozone, hydrogen peroxide, superoxide anion radicals, nitric oxide, nitrogen dioxide, peroxynitrite, dinitrogen trioxide and the like. For example, the type of active species contained in the reactive gas can be controlled by the composition of the plasma generating gas, etc.

The hydroxyl radical concentration of the reactive gas (radical concentration) is preferably 0.1 to 300 μmol/L. When the radical concentration is not less than the lower limit value, the promotion of cleaning, activation or healing of a target object selected from a cell, a living tissue and a whole body of an organism is facilitated. When the radical concentration is not more than the upper limit value, stimulus to the target surface can be reduced.

The radical concentration can be measured, for example, by the following method.

A reactive gas is applied to 0.2 mL of a 0.2 mol/L solution of DMPO (5,5-dimethyl-1-pyrroline-N-oxide) for 30 seconds. Here, the distance from the outlet to a liquid surface of the solution is set to 5.0 mm. With respect to the solution to which the reactive gas has been applied, a hydroxyl radical concentration is measured by electron spin resonance (ESR) method.

The singlet oxygen concentration of the reactive gas is preferably 0.1 to 300 μmol/L. When the singlet oxygen concentration is not less than the lower limit value, the promotion of cleaning, activation or healing of a target object such as a cell, a living tissue or a whole body of an organism is facilitated. When the singlet oxygen concentration is not more than the upper limit value, stimulus to the target surface can be reduced.

The singlet oxygen concentration can be measured, for example, by the following method.

A reactive gas is applied to 0.4 mL of a 0.1 mol/L solution of TPC (2,2,5,5-tetramethyl-3-pyrroline-3-carboxamide) for 30 seconds. Here, the distance from the outlet to a liquid surface of the solution is set to 5.0 mm. With respect to the solution to which the reactive gas has been applied, a singlet oxygen concentration is measured by election spin resonance (ESR) method.

The flow rate of the reactive gas discharged from the outlet $1a$ is preferably 1 to 10 L/min.

When the flow rate of the reactive gas discharged from the outlet $1a$ is not less than the above lower limit value, the effect of the reactive gas acting on the target surface can be sufficiently enhanced. When the flow rate of the reactive gas discharged from the outlet $1a$ is less than the above upper limit value, excessive increase in the temperature of the reactive gas at the target surface can be prevented. In addition, when the target surface is wet, rapid drying of the target surface can be prevented. Furthermore, when the target surface is an affected part of a patient, stimulus inflicted on the patient can be further suppressed.

In the reactive gas application apparatus 100, the flow rate of the reactive gas discharged from the outlet $1a$ can be adjusted by the supply amount of the plasma generating gas to the tubular dielectric 3.

The reactive gas generated by the reactive gas application apparatus 100 promotes healing of trauma and other abnormalities. The application of the reactive gas to a cell, a living tissue or a whole body of an organism can promote cleaning, activation or healing of the target part to which the reactive gas is applied.

For applying a reactive gas for the purpose of promoting healing of trauma and other abnormalities, there is no particular limitation with regard to the interval, repetition number and duration of the application. For example, when a reactive gas is applied to an affected part at a dose of 1 to 5.0 L/min, the application conditions preferred for promoting healing are as follows: 1 to 5 times per day, 10 seconds to 10 minutes for each repetition, and 1 to 30 days as total duration of treatment.

The reactive gas application apparatus 100 of the present embodiment is useful as a medical therapeutic apparatus, particularly useful as an oral cavity treatment apparatus or a dental treatment apparatus. Further, the reactive gas application apparatus 100 of the present embodiment is also suitable as an animal treatment apparatus.

A user of the reactive gas application apparatus 100 according to the present embodiment sets the application target of the target object at around the focal point F where the diameter of the guide light G on the target surface is substantially minimized. Next, the user discharges the reactive gas from the outlet $1a$ to apply the reactive gas to the target object such as an affected area of a patient. In the present embodiment, the focal point F of the guide light G is located approximately at an intersection between the guide light G and the tube axis O2 and at a preferred distance from the tip of the nozzle. Thus, a user of the reactive gas application apparatus 100 can check the discharge direction of the reactive gas by the guide light G. Further, a user can easily and surely apply the reactive gas to the application target at a suitable distance from the tip of the nozzle by setting the application target of the target object at around the focal point F where the diameter of the guide light G is substantially minimized.

The preferred distance from the nozzle tip is a distance within which the temperature, radical concentration and singlet oxygen concentration etc. of the reactive gas fall within the above-mentioned respective preferred ranges. In the present embodiment, since the reactive gas can be surely applied to the application target of the target object at a suitable distance from the nozzle tip, excessive temperature rise of the target object can be easily prevented, and the therapeutic effect of the reactive gas can be easily enhanced. Further, since the application of the reactive gas to the target object can be easily maintained at a suitable distance from the tip of the nozzle, a consistent therapeutic effect of the reactive gas can be expected so that a sufficient therapeutic effect can be enjoyed.

Second Embodiment

Hereinbelow, explanations are made with respect to a second embodiment of the present invention.

As shown in FIG. 1, the reactive gas application apparatus 200 of the present embodiment includes an application instrument 10, a power supply unit 20, a gas conduit 30, and an electrical wiring 40 as in the first embodiment. The reactive gas application apparatus 200 of the present embodiment is the same as the reactive gas application apparatus 100 of the first embodiment except that the configuration of the light source unit is different from that of the light source unit 50 in the first embodiment.

Figure 6:
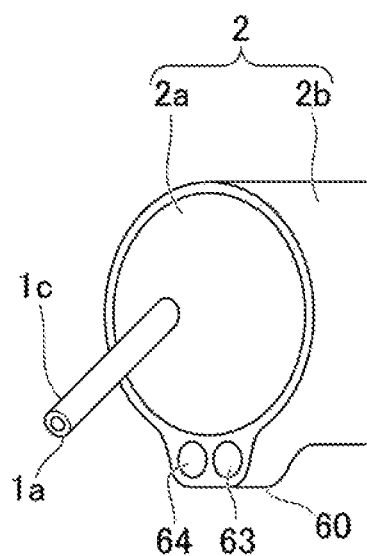
FIG. 6 is a perspective view showing a tip of the application instrument in the second embodiment.
Figure 7:
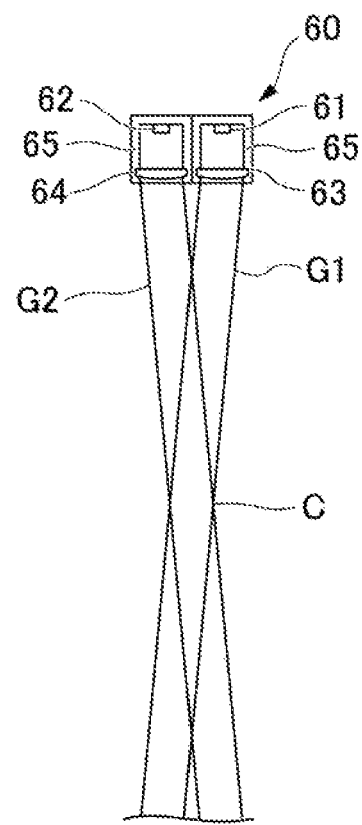
FIG. 7 is a schematic view showing a light source unit in the second embodiment and light emitted by the light source unit.

As shown in FIGS. 2, 6 and 7, the light source unit 60 in the present embodiment includes a first light emitting diode 61, a second light emitting diode 62, a first condenser lens 63, a second condenser ins 64, and a holder 65. The first light emitting diode 61 and the second light emitting diode 62 each have the same configuration as the light emitting diode 51 in the first embodiment. The first condenser lens 63 and the second condenser lens 64 each have the same configuration as the condenser lens 52 in the first embodiment. However, the first condenser lens 63 and the second condenser lens 64 condense the light emitted from the first light emitting diode 61 and the light emitted from the second light emitting diode 62 to such an extent as to impart straightness to these lights.

In the present embodiment, the emission color of the first light emitting diode 61 and the emission color of the second light emitting diode 62 are different from each other.

The first condenser lens 63 is positioned in the light emitting direction of the first light emitting diode 61. The second condensing lens 64 is positioned in the light emitting direction of the second light emitting diode 62.

The first condenser lens 63 and the second condenser lens 64 are adjacent to each other and arranged symmetrically with respect to the tube axis O1. The first condenser lens 63 and the second condenser lens 64 are arranged such that the light emitted from the first light emitting diode 61 and the light emitted from the second light emitting diode 62 intersect at a suitable distance from the nozzle tip.

Figure 8:
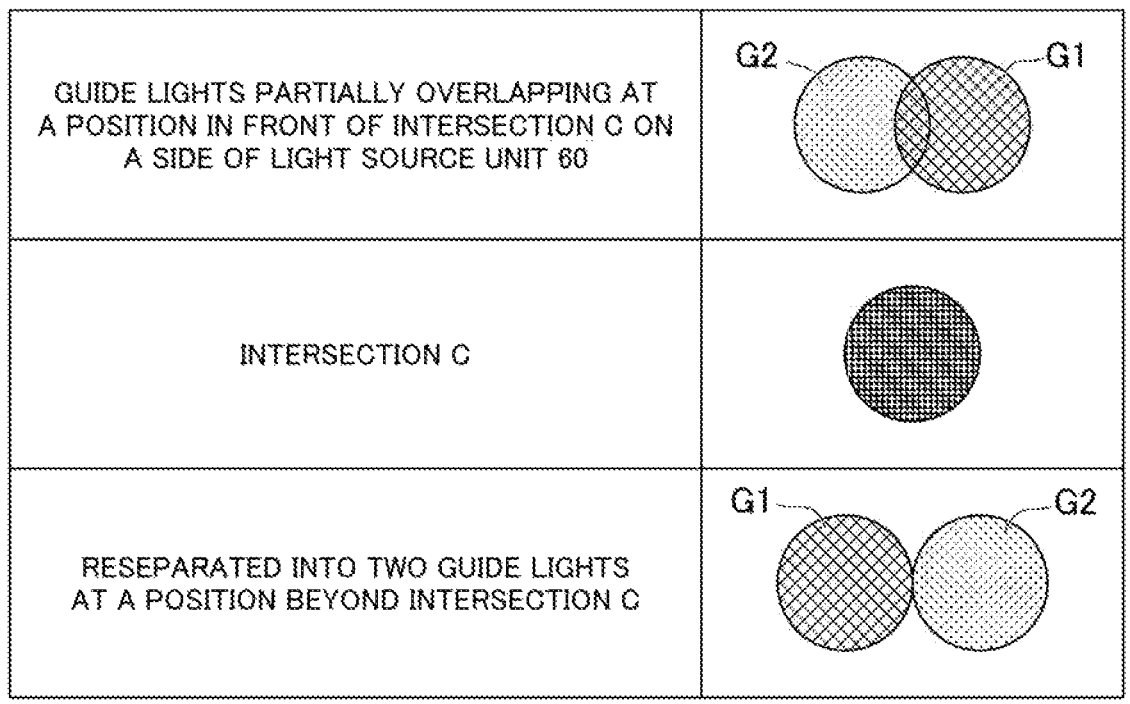
FIG. 8 is a schematic view showing light in the second embodiment, as viewed from the front of the traveling direction of the light.

In the present embodiment, there is no particular limitation with respect to the combination of the mission color of the first light emitting diode 61 and the emission color of the second light emitting diode 62. Examples of such combination include a combination of a red emission color of the first light emitting diode 61 and a blue emission color of the second light emitting diode 62. As shown in FIGS. 7 and 8, a red guide light G1 having passed through the first condenser lens 63 and a blue guide light G2 having passed through the second condenser lens 64 are initially separate lights, but eventually partially overlap with each other. Then, the guide lights G1 and G2 intersect at the intersection C and overlap, where the cross section of the light becomes substantially circular. Further, the two guide lights G1 and G2 have their colors mingled at the intersection so as to assume a purple color.

As the distance from the intersection C in a direction opposite to the light source unit 60 gradually increases, overlapping of the colors of the guide lights G1 and G2 decreases, and the light is re-separated into two different colored lights, i.e., a red light and a blue light. In the present embodiment, the intersection C is located on the tube axis O1.

In the present embodiment, the arrangement of the light source unit 60, the diameter, curvature of the curved surface and thickness of each of the first condenser lens 63 and the second condenser lens 64, and the like are adjusted, such that the intersection C of the two guide lights G1 and G2 is located approximately at a preferred distance from the nozzle tip.

A user of the reactive gas application apparatus 200 of the present embodiment sets the application target at around the intersection C of the two guide lights G1 and G2. Next, the user discharges the reactive gas from the outlet 1a and applies the reactive gas to the target object. In the present embodiment, the intersection C of the two guide lights G1 and G2 is located approximately at a preferred distance from the tip of the nozzle 1. Thus, a user of the reactive gas application apparatus 200 can check the discharge direction of the reactive gas by the guide lights G1 and G2. Further, a user can easily and surely apply the reactive gas to the application target at a suitable distance from the tip of the nozzle 1 by setting the application target at around the intersection C of the two guide lights G1 and G2.

Other Embodiments

The present invention is not limited to the above embodiment.

The shape of the inner electrode 4 of the present embodiment described above is a screw shape. However, the shape of the inner electrode is not limited as long as plasma is generated between the inner electrode and the outer electrode.

The inner electrode 4 may or may not have concavities and convexities on its surface. However, the inner electrode 4 preferably has concavities and convexities on the outer peripheral surface.

For example, the shape of the inner electrode may be a coil shape, or may be a rod shape or a cylindrical shape in which a plurality of protrusions, holes, and through holes are formed on the outer peripheral surface. The cross-sectional shape of the inner electrode is not particularly limited, and may be, for example, a circular shape such as a true circle or an ellipse, or a polygonal shape such as a square or a hexagon.

In the embodiment described above, the tube axis O2 is bent with respect to the tube axis O1. However, the tube axis O2 and the tube axis O1 may be in the same direction (i.e., the angle θ is 0°). In this instance, the orientation of the light source unit is adjusted so that the focal point of the guide light is located on the tube axis O2.

The light emitter in the above embodiment is a light emitting diode. However, in the present invention, light emitters other than light emitting diodes may also be used. As a light emitter other than the light emitting diode, a laser light generating element can be exemplified. Examples of the laser light generating element include a solid state laser, a gas laser, and a semiconductor laser.

When the use of a colored guide light is intended, it is not necessary to use a light emitting diode that emits colored light. For example, a colored guide light may be obtained by combining a white light emitting diode and a color filter.

The light source unit may not be equipped with a condenser lens. For example, when a plurality of light emitting diodes with different emission colors are used as in the second embodiment, the condenser lens may be omitted. When the emission colors of the light emitting diodes are different from each other, the position of the light source unit is adjusted such that the intersection of the two guide lights is located approximately at a preferred distance from the tip of the nozzle. The reactive gas can be easily and surely applied to the application target at a suitable distance from the tip of the nozzle by setting the application target of the target object at around the intersection of the guide lights.

Further, even when a plurality of light emitting diodes of the same color are used, the light emitting diodes may be arranged such that the intersection of the two guide lights emitted from the light emitting diodes is located approximately at a preferred distance from the tip of the nozzle. Around the intersection of the guide lights, the cross-sectional shape of the guide lights is substantially circular. Therefore, the reactive gas can be easily and surely applied to the application target at a suitable distance from the tip of the nozzle by setting the application target of the target object at around the intersection of the guide lights. For this reason, the condenser lens can be omitted.

The reactive gas application apparatus may include three or more light source units so as to emit three or more guide lights. When the number of guide lights is three or more, the accuracy of indicating the preferred distance from the nozzle tip is further enhanced; therefore, the application of the reactive gas to the target object at the preferred distance from the nozzle tip can be implemented with higher certainty.

When the application instrument is provided with two or more light source units, it is preferable that at least two light source units emitting guide lights of different colors are used.

One example of the application instrument provided with three or more source units is explained below.

Figure 9:
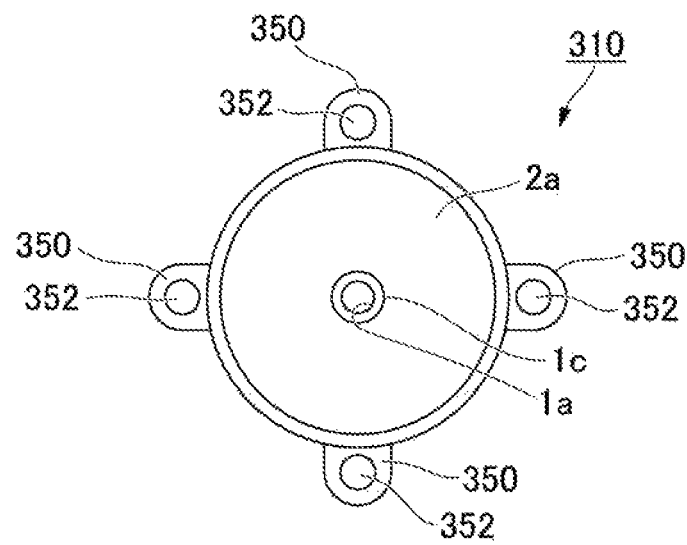
FIG. 9 is a from view showing the tip of the application instrument in another embodiment.
Figure 10:
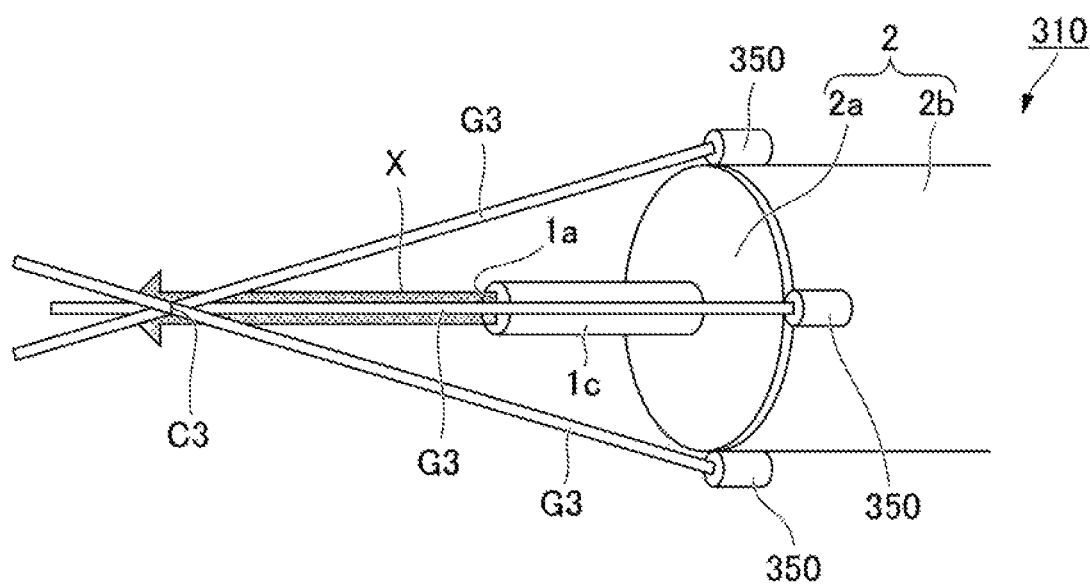
FIG. 10 is a perspective view showing the tip of the application instrument in another embodiment.

The application instrument 310 of FIGS. 9 and 10 includes discharge tube 1c that protrudes from the tip of the head 2a. In the application instrument 310, the tube axis of the discharge tube 1c is not inclined with respect to the tube axis of the body 2b.

The application instrument 310 includes four light source units 350 at the periphery of the head 2a. The four light source units 350 are located at intervals of 90° with the irradiation tube 1c being the center thereof. Each light source unit 350 includes a light emitter 352. The light emitter 352 may be, for example, a light emitting diode. The light emitted from the light emitting diode hardly diffuses. For this reason, when a light emitting diode is used as the light emitter 352, the light source unit 350 may not include the condenser lens. The color tones of the four light emitters 352 may be the same or may be different from each other. However, the color tones of the four light emitters 352 are preferably the same. When the color tones of the four light emitters 352 are the same, the visibility on the illuminated surface can be further enhanced.

A user of the reactive gas application apparatus in the application instrument 310 sets the application target at around the intersection C of the four guide lights G3. Next, the user discharges the reactive gas X from the outlet 1a and applies the reactive gas X to a target surface.

In the present embodiment, the intersection C of the four guide lights G3 is located approximately at a preferred distance from the tip of the nozzle. Thus, a user of the reactive gas application apparatus can check the discharge direction of the reactive gas by the guide lights G3. Further, a user can easily and surely apply the reactive gas to the application target at a suitable distance from the tip of the nozzle by setting the application target at around the intersection C of the four guide lights G3.

Furthermore, the illuminance is high at the intersection C1 of the four guide lights G3. Therefore, a user of the reactive gas application apparatus can visually recognize the target surface with more case.

In the above embodiment, the light source unit is located outside the cowling in the bending direction of the nozzle. However, the position of the light source unit is not particularly limited. The application instrument may have a light source unit inside the cowling so as to allow the guide light to pass through the second reactive gas flow path. When the guide light is passed through the second reactive gas flow path, it is possible to visually recognize the advancing direction of the discharged reactive gas. When the guide light is passed through the second gas flow path, it is preferable that the guide light is a laser light having high straightness. When the guide light is passed through the second gas flow path, it is preferable not to use a condenser lens.

Further, when the application instrument is configured such that the light source unit is provided inside the cowling as described above, light is not blocked by teeth, lips, tongue, etc. when the head 2a is inserted into the oral cavity, and therefore, the freedom in manipulating the application instrument during the treatment is enhanced. Also, for obtaining the same effect as mentioned above, the application instrument may be configured such that the light source unit is provided on the nozzle, or is provided outside the cowling at a position as close to the tube axis O2 as possible (for example, at a position where the distance from the tube axis O2 to the center of the light emitted by the light source when the nozzle is viewed from its front (tip) is preferably 20 mm or less, more preferably 15 mm or less, still more preferably 10 mm or less, still more preferably 5 mm or less, and most preferably 1 mm or less). Alternatively, when it is difficult to employ the above-mentioned configurations, the application instrument may be configured such that only the light source unit or the light emitter is provided outside the cowling at a position away from the tube axis O2 while providing a condenser lens on the nozzle so as to have light from the light emitter refracted by the condenser lens on the nozzle and converged to the focal point F at a desired position. Further, in another preferable embodiment of the present invention, the application instrument may be configured such that the light emitter provided outside the cowling and the condenser lens provided on the nozzle are connected with each other through an optical fiber. In this instance, both of the freedom in manipulating the application instrument and the ease in designing the application instrument can be simultaneously improved.

The electrodes contained inside the application instrument need not be those shown in the above embodiments, and may be, for example, a pair of plate-like or columnar electrodes facing each other along the body of the application instrument.

In the supply unit in the above embodiments, the pump for supplying the plasma generating gas to the application instrument and the power supply unit are accommodated in the same housing, but the pump and the power supply unit may be installed separately. Further, the plasma generating gas may be supplied to the application instrument 10 by the pressure in the supply source of the plasma generating gas without installing a pump in the supply unit.

DESCRIPTION OF THE REFERENCE SIGNS

1 Nozzle
10,310 Application instrument
12 Plasma generating unit
50,60,350 light source unit
51 Light emitting diode
52 Condenser lens
61 First light emitting diode
62 Second light emitting diode
63 First condenser lens
64 Second condenser lens
100,200 Reactive gas application apparatus
352 Light emitter
G,G1,G2,G3 Guide light

The invention claimed is:
1. A reactive gas application apparatus comprising:
a plasma generating unit comprising a tubular dielectric, an inner electrode, and an outer electrode,
a nozzle for discharging a reactive gas activated by plasma generated in the plasma generation unit,
a light source unit for emitting light toward a position ahead of a tip of the nozzle, and
a control unit configured to synchronize plasma generation in the plasma generation unit and light emission in the light source unit.
2. The reactive gas application apparatus according to claim 1, wherein the light source unit emits light having a focal point.

3. The reactive gas application apparatus according to claim 1, wherein the light source unit comprises a light emitter and a condenser lens positioned in a light emission direction of the light emitter.

4. The reactive gas application apparatus according to claim 1, which has two or more light source units.

5. The reactive gas application apparatus according to claim 4, wherein the two or more light source units emit respectively different colored lights, and the different colored lights overlap at a predetermined position.

6. The reactive gas application device according to claim 1, which is a medical therapeutic apparatus.

7. The reactive gas application apparatus according to claim 1, wherein the inner electrode comprises a shaft portion extending in a tube axis direction of the tubular dielectric and a screw thread on an outer peripheral surface of the shaft portion.

8. The reactive gas application apparatus according to claim 1,
wherein the control unit is configured to detect electric conduction for applying a voltage between the inner electrode and the outer electrode, and allow the light source unit to emit light while the electric conduction is being detected, or to detect plasma generated in an internal space of the reactive gas application apparatus, and allow the light source unit to emit light while plasma generation is being detected.

* * * * *